United States Patent
Ikeda et al.

[11] Patent Number: 5,985,116
[45] Date of Patent: Nov. 16, 1999

[54] BIOSENSOR

[75] Inventors: Shin Ikeda, Katano; Toshihiko Yoshioka; Shiro Nankai, both of Hirakata, all of Japan

[73] Assignee: Matsushita Electric Industrial Co., Ltd., Osaka, Japan

[21] Appl. No.: 08/989,426

[22] Filed: Dec. 12, 1997

[30] Foreign Application Priority Data

Dec. 24, 1996 [JP] Japan .................................. 8-343568

[51] Int. Cl.[6] .................................................. G01N 27/26
[52] U.S. Cl. ...................................... 204/403; 204/290 R
[58] Field of Search .............................. 204/403; 435/817

[56] References Cited

U.S. PATENT DOCUMENTS

| | | | |
|---|---|---|---|
| 5,512,159 | 4/1996 | Yoshioka et al. | 204/403 |
| 5,628,890 | 5/1997 | Carter et al. | 204/403 |
| 5,658,444 | 8/1997 | Black et al. | 204/415 |
| 5,710,011 | 1/1998 | Forrow et al. | 435/25 |
| 5,849,174 | 12/1998 | Sanghera et al. | 205/775 |

FOREIGN PATENT DOCUMENTS

| | | |
|---|---|---|
| 0537761 | 10/1992 | European Pat. Off. . |
| 0735363 | 10/1992 | European Pat. Off. . |
| 593096 A2 | 4/1994 | European Pat. Off. . |
| 0732406 | 7/1995 | European Pat. Off. . |
| 03202764 | 4/1991 | Japan . |

*Primary Examiner*—T. Tung
*Assistant Examiner*—Alex Noguerola
*Attorney, Agent, or Firm*—McDermott, Will & Emery

[57] ABSTRACT

The biosensor of the present invention has a reaction layer that contains at least an oxidoreductase and an electron acceptor and is formed on an electrode system including a working electrode and a counter electrode on a base plate. The working electrode, the counter electrode, and lead conductors connecting with these electrodes are made of carbon. The counter electrode is formed in a substantially C shape, and the working electrode is arranged in a recess of the substantially C-shaped counter electrode. An insulating layer surrounds the counter electrode and the working electrode. A cover member with a groove is combined with the base plate to define a sample supply channel that is formed therebetween and runs toward the electrode system. The groove extends from one end of the base plate and passes over the electrode system, and the insulating layer extends to an air hole formed in a terminal of the groove of the cover member. This arrangement prevents exposure of part of the lead conductor connecting with the working electrode to the sample solution and development of an error in measurement.

4 Claims, 2 Drawing Sheets

BIOSENSOR

BACKGROUND OF THE INVENTION

The present invention relates to a biosensor that is manufactured at low cost and can readily determine a specific compound in a sample at high speed and with high accuracy.

Proposed methods of quantitative analysis for determining sugars, such as sucrose and glucose, utilize a technique like polarimetry, colorimetry, reductometry, or chromatography. These methods, however, have relatively low specificity to the sugars and thereby poor accuracy. For example, the polarimetry is simple in operation but significantly affected by the peripheral temperature. Namely the polarimetry is not suitable for domestic use, in which generally non-skilled people determine sugars.

Various types of biosensors recently developed utilize the specific catalytic activities of enzymes.

The following describes determination of glucose as one example of quantitative analysis of a substrate in a sample solution. A known technique of electrochemical determination of glucose uses glucose oxidase (EC1.1.3.4: hereinafter referred to as GOD) and either an oxygen electrode or a hydrogen peroxide electrode (see, for example, 'Biosensor' ed. by Shuichi SUZUKI, Kodan-sha).

GOD uses oxygen as an electron acceptor and selectively oxidizes the substrate or β-glucose to D-glucono-δ-lactone. In the presence of oxygen, the oxidation reaction by GOD reduces oxygen to hydrogen peroxide. The decrease in amount of oxygen may be measured by the oxygen electrode, or otherwise, the increase in amount of hydrogen peroxide may be measured by the hydrogen peroxide electrode. Both the decrease in amount of oxygen and the increase in amount of hydrogen peroxide are proportional to the content of glucose in the sample solution, so that measurement of the decrease in oxygen or the increase in hydrogen peroxide determines glucose.

As presumable from its reaction process, however, this known technique has some drawbacks: the results of measurement are significantly affected by the concentration of oxygen included in the sample solution; and the absence of oxygen in the sample solution makes the measurement itself impossible.

A novel type of glucose sensor developed to remove such drawbacks uses potassium hexacyanoferrate(III), one of organic compounds such as ferrocene derivatives and quinone derivatives, or a metal complex as the electron acceptor, instead of oxygen. This novel type of sensor oxidizes the reductant of the electron acceptor obtained as a result of the enzyme reaction on the electrode and determines the concentration of glucose included in the sample solution based on the observed oxidation current. Application of the organic compound or metal complex, instead of oxygen, as the electron acceptor enables a known quantity of GOD and the electron acceptor to be accurately carried on the electrode in a stable state to form a reaction layer. The reaction layer that is substantially in a dry state may be integrated with the electrode system. Disposal glucose sensors based on this technique have drawn much attention recently.

This disposal glucose sensor enables the user to readily determine glucose simply by introducing a sample solution into the sensor detachably connected to a measurement device. This technique is applicable to not only determination of glucose but determination of another substrate included in the sample solution.

The technique of utilizing such an electron acceptor and integrating the electrode system with the reaction layer enables simple electrochemical qualitative evaluation of the substrate. Lead conductors composed of a metal, such as palladium or silver, undesirably increase the manufacturing cost. Carbon lead conductors, on the other hand, require a relatively large width to depress an increase in electrical resistance. The large width of lead conductors causes part of a lead conductor led from a working electrode to be exposed to a sample solution, which may result in a positive error in measurement.

SUMMARY OF THE INVENTION

The present invention accordingly provides a biosensor comprising:

a base plate with a pair of carbon lead conductors formed thereon, the carbon lead conductors having one end formed as an electrode system and the other end as an electrical connection to a measurement device;

a cover member with a groove arranged on the base plate to define a sample supply channel that is formed therebetween and runs from one end of the base plate to the electrode system;

an insulating layer for surrounding the electrode system on the base plate; and a reaction layer containing at least an oxidoreductase and an electron acceptor and being formed on the electrode system surrounded by the insulating layer, wherein the electrode system includes a substantially C-shaped counter electrode and a working electrode located in a recess of the substantially C-shaped counter electrode, the groove extending from the end of the base plate and passing over the electrode system, and the insulating layer extending to an air hole formed in a terminal of the groove of the cover member.

It is preferable that the electrical resistance between the electrode system and the electrical connection is not greater than 10 kΩ.

It is also preferable that a lecithin layer is formed in the groove of the cover member or more specifically over the whole length of the groove.

It is further preferable that the reaction layer includes a hydrophilic polymer.

While the novel features of the invention are set forth particularly in the appended claims, the invention, both as to organization and content, will be better understood and appreciated, along with other objects and features thereof, from the following detailed description taken in conjunction with the drawings.

DETAILED DESCRIPTION OF THE INVENTION

The biosensor of the present invention is described in detail with the accompanying drawings.

Figure 1:
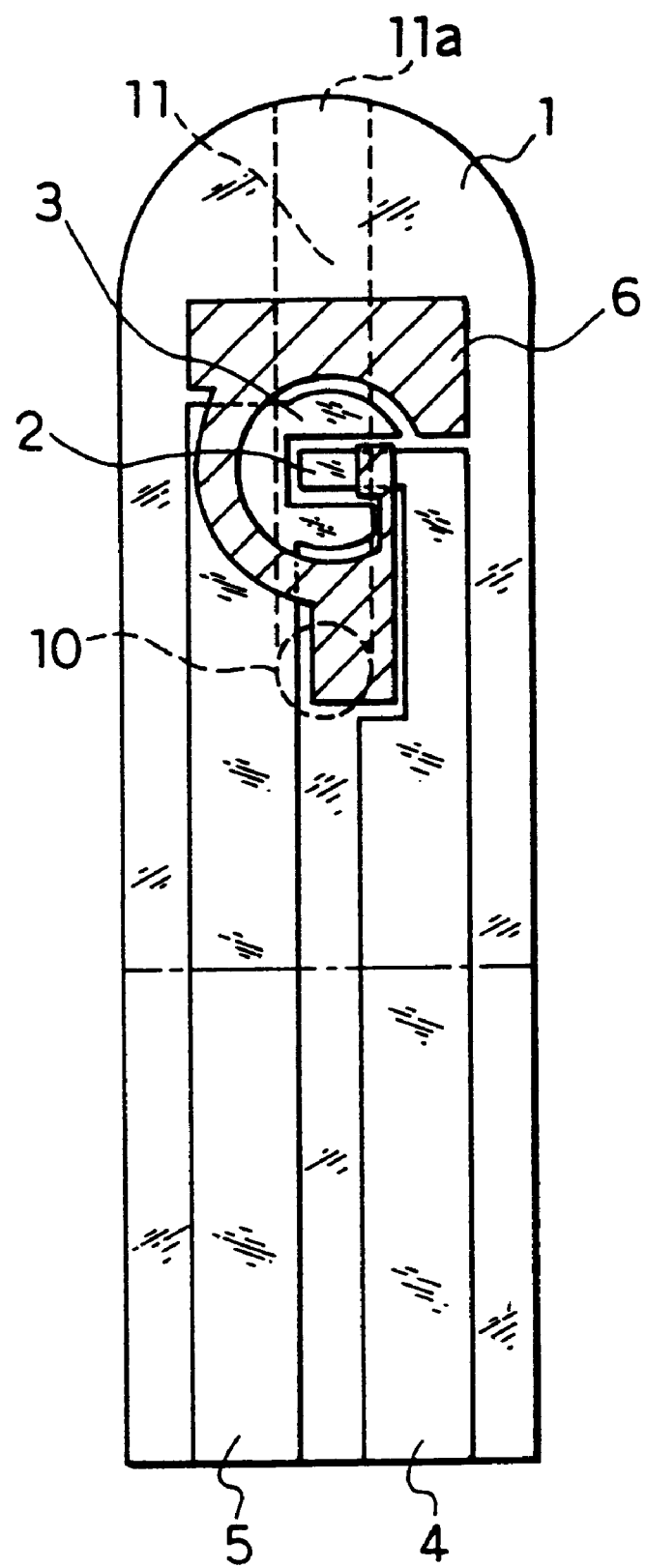
FIG. 1 is a plane view illustrating a base plate with an electrode system applied for a glucose sensor in accordance with one embodiment of the present invention.
Figure 2:
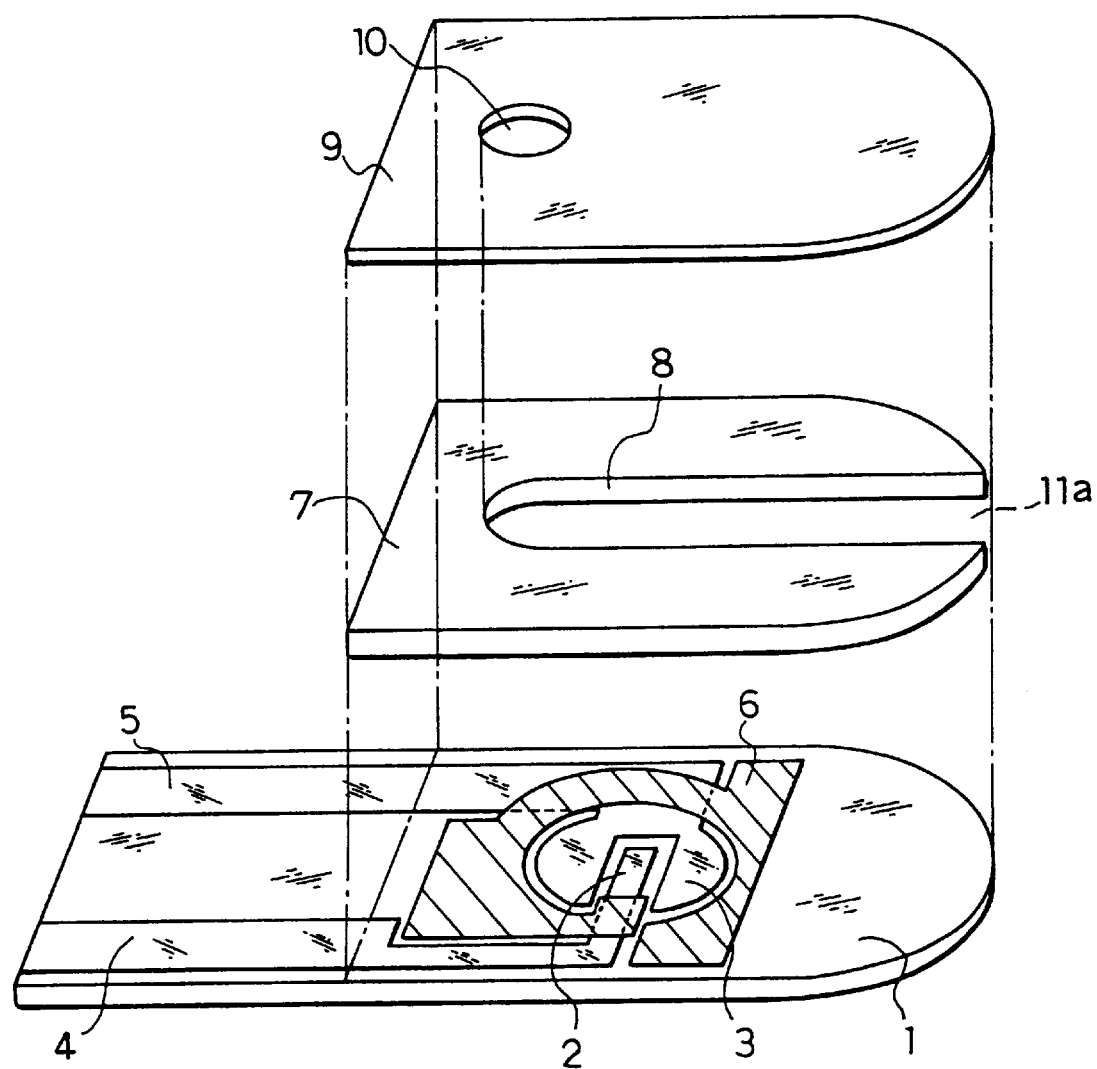
FIG. 2 is a decomposed perspective view illustrating the glucose sensor of FIG. 1 except a reaction layer.

FIG. 1 is a plan view illustrating a base plate of a biosensor embodying the present invention, and FIG. 2 is a decomposed perspective view illustrating the biosensor of FIG. 1 except a reaction layer.

A working electrode 2, a counter electrode 3, and lead conductors 4 and 5 connecting with the respective electrodes are formed on an electrically insulating base plate 1. The base plate 1 is composed of polyethylene terephthalate, while the other elements 2, 3, 4, and 5 are all composed of carbon. These electrodes and lead conductors 2, 3, 4, and 5 are simultaneously formed by one-time screen printing of a binder-containing carbon paste. The counter electrode 3 is formed in a substantially C shape, and the working electrode 2 is arranged in the recess of the substantially C-shaped counter electrode 3. The lead conductors 4 and 5 connecting with these electrodes 2 and 3 extend to one end of the base plate 1, which functions as an electrical connection to a measurement device.

An electrically insulating layer 6 that is formed by printing an electrically insulating paste is further arranged on the base plate 1 with the working electrode 2, the counter electrode 3, and the lead conductors 4 and 5 formed thereon. The electrically insulating layer 6 separates the working electrode 2 and the counter electrode 3 from the lead conductors 4 and 5 and defines the exposed areas of the working electrode 2 and the counter electrode 3. It is preferable that the inner side of the electrically insulating layer 6 is formed in a substantially circular shape except a part corresponding to the working electrode 2.

A reaction layer is subsequently formed on the base plate 1 with the electrode system. The reaction layer may be readily prepared by adding solutions of required reagents dropwise onto the electrode system and drying them as discussed later. Since the carbon electrodes 2 and 3 are surrounded by the electrically insulating layer 6, the reaction layer can advantageously be formed in a restricted manner only on a specified area. In other words, the electrically insulating layer 6 prevents the solutions for forming the reaction layer from being spread to the lead conductors 4 and 5. This structure enables a homogeneous reaction layer to be prepared with high reproducibility.

A cover member is combined with the base plate 1 to define a sample supply channel formed therebetween. The cover member includes a spacer 7 with a slit 8 open to one end and a cover 9 having an air hole 10 arranged at a position corresponding to a terminal of the slit 8. The spacer 7 and the cover 9 are composed of the same insulating material as that of the base plate 1. A biosensor is completed by bonding the base plate 1, the spacer 7, and the cover 9 to one another in such a manner that the respective portions shown by the one-dot chain lines in FIG. 2 are matched.

In this biosensor, the sample supply channel is formed in a portion 11 surrounded by the broken line in FIG. 1 on the base plate 1. The sample supply channel 11 corresponds to the slit 8 of the spacer 7 and extends over the electrode system. When an opening 11a of the sample supply channel 11 is exposed to a sample solution, the sample solution sucked by the capillary action runs through the sample supply channel 11 toward the air hole 10 and reaches the electrode system to react with the reagents of the reaction layer thereon.

As clearly shown in FIG. 1, the restricted working electrode 2 and counter electrode 3 constituting the electrode system and the electrically insulating layer 6 surrounding the electrode system are exposed on the base plate 1 facing the sample supply channel 11. The lead conductor 4 separated from the working electrode 2 by the electrically insulating layer 6 is made apart from the sample supply channel 11 by the electrically insulating layer 6. This structure effectively prevents a measurement error due to exposure of the lead conductor 4 of the working electrode 2 to the sample solution. Although part of the lead conductor 5 of the counter electrode 3 is exposed to the sample supply channel 11, the exposure of the part to the sample solution does not affect the measurement result.

Application of a paste on the working electrode, the counter electrode, and the corresponding lead conductors, which are all made of carbon, to form an electrically insulating layer often causes an increase in electrical resistance. This may be ascribed to penetration of the paste into the carbon layer. It is accordingly preferable that the electrically insulating layer for separating the working electrode and the counter electrode from their lead conductors is formed in a restricted area on the carbon printed layer as shown in FIG. 1.

In the examples discussed below, carboxymethylcellulose is used as the hydrophilic polymer. Other available hydrophilic polymers to form a hydrophilic polymer layer include hydroxyethylcellulose, hydroxypropylcellulose, methylcellulose, ethylcellulose, ethylhydroxyethylcellulose, carboxymethylethylcellulose, poly(vinyl pyrrolidone), poly(vinyl alcohol), polyamino acids such as polylysine, poly(styrene sulfonate), gelatin and its derivatives, acrylic acid and its derivatives, methacrylic acid and its derivatives, starch and its derivatives, and maleic anhydride and its derivatives. Especially preferable are carboxymethylcellulose, include hydroxyethylcellulose, hydroxypropylcellulose, methylcellulose, ethylcellulose, ethylhydroxyethylcellulose, and carboxymethylethylcellulose. Polyamino acids such as polylysine, poly(vinyl alcohol), and poly(styrene sulfonate) are also usable.

The oxidoreductase included in the reaction layer should be varied according to the substrate to be measured. Available oxidoreductase include fructose dehydrogenase, glucose oxidase, alcohol oxidase, lactate oxidase, cholesterol oxidase, xanthine oxidase, and amino acid oxidase.

Available examples of the electron acceptor include potassium hexacyanoferrate(III), p-benzoquinone, phenazine methosulfate, methylene blue, and ferrocene derivatives. Oxygen used as the electron acceptor also ensures the sensor response. One or a plurality of these alternatives may be used for the electron acceptor.

The enzyme and the electron acceptor may be dissolved in the sample solution or may not be dissolved in the sample solution when the reaction layer is fixed to the base plate. In case that the enzyme and the electron acceptor are fixed, it is preferable that the reaction layer contains the hydrophilic polymer.

The reaction layer may further contain a pH buffer. Available pH buffers include potassium dihydrogenphosphate-dipotassium phosphate, potassium dihydrogenphosphate-disodium phosphate, sodium dihydrogenphosphate-dipotassium phosphate, sodium dihydrogenphosphate-disodium phosphate, citric acid-disodium phosphate, citric acid-dipotassium phosphate, citric acid-trisodium citrate, citric acid-tripotassium citrate, potassium dihydrogencitrate-sodium hydroxide, sodium dihydrogencitrate-sodium hydroxide, sodium hydrogenmaleate-sodium hydroxide, potassium hydrogenphthalate-sodium hydroxide, succinic acid-sodium tetraborate, maleic acid-tris(hydroxymethyl)aminomethane, tris(hydroxymethyl)aminomethanetris(hydroxymethyl) aminomethane hydrochloride, [N-(2-hydroxyethyl) piperazine-N'-2-ethanesulfonic acid]-sodium hydroxide, [N-tris(hydroxymethyl)methyl-2-aminoethanesulfonic acid]-sodium hydroxide, and [piperazine-N,N'-bis(2-ethanesulfonic acid)]-sodium hydroxide.

Although the following examples illustrate specific printing patterns of carbon paste and an electrically insulating paste, the patterns are not restricted to these examples.

The features and the advantages of the present invention will become more apparent through the description of the preferred examples.

EXAMPLE 1

A glucose sensor is described below as a typical example of biosensors.

The glucose sensor was manufactured in the following manner. As shown in FIG. 1, the working electrode 2, the counter electrode 3, the lead conductors 4 and 5 respectively connecting with the electrodes 2 and 3, and the electrically insulating layer 6 were formed on the base plate 1.

An aqueous solution containing GOD as the enzyme and potassium hexacyanoferrate(III) as the electron acceptor was added dropwise onto the electrode system consisting of the working electrode 2 and the counter electrode 3 and dried to form a reaction layer. Arrangement of the electrically insulating layer 6 surrounding the electrode system as shown in FIG. 1 effectively prevents the solution for forming the reaction layer from being spread to the lead conductors 4 and 5.

In order to ensure smooth supply of the sample solution to the reaction layer, lecithin dissolved in an organic solvent, for example, toluene, was spread over the reaction layer and dried to form a lecithin layer. A glucose sensor was then completed by bonding the cover 9 and the spacer 7 to the base plate 1.

An aqueous glucose solution (3 μl) as the sample solution was supplied through an opening 11a of the sample supply channel 11 of this sensor.

Simultaneously with supply of the sample solution, the reaction layer on the electrode system was dissolved in the sample solution. After 55 seconds elapsed, a predetermined potential was applied to the working electrode 2 with respect to the reference counter electrode 3. The electric current was measured after 5 seconds. The reaction of glucose with hexacyanoferrate(III) ions and GOD oxidizes glucose to gluconolactone while reducing hexacyanoferrate(III) ions to hexacyanoferrate(II) ions. The electric current for oxidizing the hexacyanoferrate(II) ion is obtained as a response. The observed electric current depended upon the concentration of glucose included in the sample solution.

EXAMPLE 2

An aqueous solution of sodium carboxymethylcellulose (hereinafter referred to as CMC) was added dropwise onto the electrode system of the base plate prepared in the same manner as Example 1 and dried to form a CMC layer. An aqueous solution containing GOD as the enzyme and potassium hexacyanoferrate(III) as the electron acceptor was subsequently added dropwise onto the CMC layer and dried to form a reaction layer.

The spacer 7 and the cover 9 were bonded to each other. Lecithin dissolved in an organic solvent, for example, toluene, was added dropwise into an area of the groove in the cover member defined by the slit 8 of the spacer 7 to face the electrode system and dried to form a lecithin layer. The lecithin layer formed in the cover member ensures smooth supply of the sample solution to the reaction layer. Direct addition of the lecithin solution of organic solvent onto the reaction layer causes the solution to spread over the carbon lead conductor and may increase the electrical resistance between the electrode system and the electrical connection. Formation of the lecithin layer in the cover member, on the other hand, solves this problem.

A glucose sensor was completed by bonding the integral cover member consisting of the spacer 7 and the cover 9 with the lecithin layer to the base plate 1.

An aqueous glucose solution (3 μl) as the sample solution was supplied through the opening of the sample supply channel 11 of this sensor. Simultaneously with supply of the sample solution, the reaction layer on the electrode system was dissolved in the sample solution. After 55 seconds elapsed, a predetermined potential was applied to the working electrode 2 with respect to the reference counter electrode 3. The electric current was measured after 5 seconds. The observed electric current depended upon the concentration of glucose included in the sample solution.

In this example, the reaction layer contained CMC, which interfered with adsorption of the enzyme to the surface of the electrodes. This led to the better response.

EXAMPLE 3

A glucose sensor was manufactured in the same manner as Example 2, except a variation in thickness of the carbon layer. A plurality of electrodes having the electrical resistances between the working electrode and the electrical connection and between the counter electrode and the electrical connection in a range of 5 to 15 kΩ were prepared by varying a thickness of the carbon layer.

The sensor response was evaluated in the same manner as Example 2. The electrodes having the resistance of not greater than 10 kΩ gave the favorable sensor response.

As discussed above, the present invention provides a biosensor that is manufactured at low cost and can readily determine a specific compound in a sample at high speed and with high accuracy.

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications as fall within the true spirit and scope of the invention.

We claim:

1. A biosensor comprising:
   a base plate with a pair of carbon lead conductors formed thereon, said carbon lead conductors having one end formed as an electrode system and the other end as an electrical connection to a measurement device;
   a cover member with a groove arranged on said base plate to define a sample supply channel that is formed therebetween and runs from one end of said base plate to said electrode system;
   an insulating layer for surrounding said electrode system on said base plate; and
   a reaction layer containing at least an oxidoreductase and an electron acceptor and being formed on said electrode system surrounded by said insulating layer, wherein said electrode system comprises a substantially C-shaped counter electrode and a working electrode located in a recess of said substantially C-shaped counter electrode, said groove extending from said one end of said base plate and passing over said electrode system, and said insulating layer extending to an air hole formed in a terminal of said groove of said cover member, wherein the insulating layer covers the carbon lead conductors only at localized portions in an area that surrounds the electrode system.

2. The biosensor in accordance with claim 1, wherein electrical resistance between said electrode system and said electrical connection is not greater than 10 kΩ.

3. The biosensor in accordance with either one of claims 1 and 2, wherein a lecithin layer is formed in said groove of said cover member.

4. The biosensor in accordance with claim 1, wherein said reaction layer comprises a hydrophilic polymer.

* * * * *